United States Patent [19]

Hein et al.

[11] Patent Number: 4,808,407
[45] Date of Patent: Feb. 28, 1989

[54] WATER-SOLUBLE COPPER SALTS

[75] Inventors: Richard W. Hein, Hudson; Anthony Alkaitis, deceased, late of Cleveland Hts., both of Ohio, by Audrey V. Alkaitis, executrix

[73] Assignee: Mooney Chemicals, Inc., Cleveland, Ohio

[21] Appl. No.: 85,453

[22] Filed: Aug. 14, 1987

[51] Int. Cl.$^4$ .................. A01N 59/20; A01N 55/02
[52] U.S. Cl. .................... 424/141; 514/500; 260/414; 556/114; 556/115; 106/18.32; 106/15.05
[58] Field of Search ............. 260/414; 106/18.32, 106/15.05; 556/115; 514/71, 424, 499, 500; 252/389.53, 400.53; 424/141

[56] References Cited

U.S. PATENT DOCUMENTS

| | | | |
|---|---|---|---|
| 2,075,230 | 3/1937 | Schatz | 134/57 |
| 2,364,391 | 12/1944 | Schiller | 106/243 |
| 2,423,619 | 7/1947 | Roon | 167/22 |
| 3,262,846 | 7/1966 | Ercegovich | 167/42 |
| 3,333,942 | 8/1967 | Hartley et al. | 71/93 |
| 4,001,400 | 1/1977 | Hager | 424/134 |
| 4,193,993 | 3/1980 | Hilditch | 424/141 |
| 4,324,797 | 4/1982 | Suzuki | 424/287 |
| 4,507,152 | 3/1985 | Collins et al. | 106/18.31 |
| 4,528,185 | 7/1985 | Kraft et al. | 424/81 |
| 4,622,248 | 11/1986 | Leach et al. | 427/440 |

FOREIGN PATENT DOCUMENTS 519146 4/1977 Australia .
WO8504668 11/1985 World Int. Prop. O. ....... 106/15.05

OTHER PUBLICATIONS

Australian Patent Abstract 16677/83, Parisse and DeReure, Publication Date of Australian Reference: 7/83.
H. Greaves et al, "Studies of Preservative Treatments for Hardwoods in Ground Contact", Holzforschung, 36 (1982) 225–231.

*Primary Examiner*—H. M. S. Sneed
*Assistant Examiner*—Elizabeth Irzinski
*Attorney, Agent, or Firm*—Renner, Otto, Boisselle & Sklar

[57] ABSTRACT

An improved process for preparing water-soluble copper salts of carboxylic acids is described. More particularly, the improved process comprises the steps of
(A) providing a mixture comprising
  (A-1) as a copper source, copper metal, a copper oxide or mixtures thereof,
  (A-2) at least one organic monocarboxylic acid containing about 10 to about 30 carbon atoms,
  (A-3) at least one alkanolamine compound characterized by the formula $R_1(R_2)NH$ 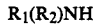

wherein $R_1$ is a hydroxyalkyl group and $R_2$ may be hydrogen or a hydroxyalkyl group, and
  (A-4) water,
(B) treating the mixture with oxygen at a temperature up to about the reflux temperature of the mixture until the desired water-soluble copper salt is obtained, and
(C) recovering the copper salt as an aqueous solution.

The mixture (A) can be modified to include one or more dyes to produce colored solutions of the water-soluble metal salts. The water-soluble copper salts prepared in accordance with the method of the invention are useful in a variety of applications, particularly as a preservative for wood. The invention also relates to wood which has been treated with the water-soluble copper salts of the present invention.

34 Claims, No Drawings

WATER-SOLUBLE COPPER SALTS

FIELD OF THE INVENTION

The present invention relates to water-soluble copper salts of carboyxlic acids and to a method of preparing such salts. The invention also relates to methods of preserving wood and to the wood treated in accordance with the method of the present invention.

BACKGROUND OF THE INVENTION

In order to prevent decay of wood and timbers, and thereby increase their life, it is common practice to impregnate the wood or timbers with a preservative such as creosote, mixtures of inorganic compounds which are dissolved or dispersed in water, or certain organic compounds which are dissolved in petroleum distillates or dispersed in water. The protection afforded by the application of these materials is dependent upon deep and reasonably uniform penetration of the wood or timber by the preservative material. Wood preservatives such as those described above have been applied to the wood as solutions, emulsions, pastes or dispersions in liquid hydrocarbons and/or aqueous systems. In many applications, the use of aqueous systems is preferred over liquid hydrocarbons because of the odors, flammability and often toxic nature of the liquid hydrocarbons. In some instances, the use of liquid hydrocarbons for preparing wood-impregnated solutions may result in the deposit an oily surface on the wood which is difficult to paint. Also, liquid hydrocarbons are flammable materials requiring special handling and safety precautions which add to the cost of the wood treatment.

Wood treated with organic preservatives dissolved in petroleum distillates have the same disadvantages as wood treated with hydrocarbons. Using low boiling petroleum distillates, such as mineral spirits, as solvents, fails to eliminate the disadvantages completely. Prolonged air seasoning after treatment frequently is required to permit sufficient evaporation of the solvent if the wood is to be painted. During this period of air seasoning, a portion of the preservative can migrate to the surface of the wood with the solvent, and thus, the retention of the preservative in the wood may be reduced below that contemplated for the treatment.

U.S. Pat. No. 2,423,619 describes the preparation of aqueous ammonia solutions of copper soaps by reaction of copper hydroxide or copper carbonate with naphthenic acid in the presence of ammonia.

U.S. Pat. No. 4,507,152 describes aqueous compositions having fungicidal and insecticidal properties which can be used in the treatment of wood. The aqueous compositions comprise oil-soluble metal salts of carboxylic acids, halopyridyl phosphates and surfactants. Aqueous ammoniacal solutions of fatty acid salts are described in U.S. Pat. No. 4,001,400, and aqueous solutions of metal salts of carboxylic acids and ammonia and/or ammonium compounds are described in U.S. Pat. No. 4,193,993 (Re 31,576). The ammonia and/or ammonium compounds are utilized to maintain the metal salt in solution.

Suzuki (U.S. Pat. No. 4,324,797) describes water-soluble metal soap compositions comprising the combination of a metal soap of the general formula $(RCOO)_xM$ wherein M is lithium or a non-alkali metal atom, x represents its valency, and R represents a hydrocarbon group having from 4 to 20 carbon atoms, and a chelating agent such as polybasic carboxylic acids, polyamino carboxylic acid salts, amines, etc. Conventional surfactants may be added to the aqueous solutions of the metal soap compositions. Among the amines disclosed as being useful chelating agents are polyamines such as ethylene diamine, alkanol amines such as triethanolamine, monoethanolamine, etc. Water-soluble metal soap compositions are obtained by preparing a mixture of the metal soap and the chelating agent and then heating the mixture to form the water-soluble composition.

U.S. Pat. No. 2,364,391 describes the preparation of metallic soaps useful for treating fabrics wherein metal soaps such as copper naphthenate, zinc naphthenate, etc., are complexed with ammonia and small amounts of alkanol amines are added to the ammonia complex. Examples of alkanol amines include mono-, di- and triethanol amine, and monoisopropanol amine. The alkanol amine is added to the treating solution to delay the precipitation of the soap which otherwise results when the ammonia evaporates. U.S. Pat. No. 3,262,846 describes oil-soluble copper salts emulsified in water. Diverse materials are disclosed as being useful as emulsifiers, and among the emulsifiers disclosed are the ethanolamines.

Hydrocarbon-soluble, water-insoluble salts such as copper naphthenates are described in U.S. Pat. No. 2,075,230. The hydrocarbon-soluble salts are obtained by reacting an organic acid or alkali metal salts of organic acids with a base metal compound capable of forming water-insoluble salts with said acids. Thus, the base metal compounds may be oxides or hydroxides of alkaline earth metals or heavy metals. The reaction is carried out in the presence of amines, and a wide variety of amines are disclosed as being useful. Alkylol amines such as mono-, di- and triethanolamines or propanol amines are described as being useful amines.

It also is desirable to produce wood products that are aesthetically acceptable, yet protected from wood-destroying organisms. Wood that is colored and preserved is desirable for the home, and can be used in siding, fencing and decking. Unfortunately, many of the preservative solutions used heretofore to preserve wood from wood-destroying organisms impart their own color to the wood. In many cases, the coloration imparted by the preserving solution is less than aesthetically pleasing. As mentioned above, attempts to impart desirable color by painting preserved wood often is unacceptable because it is often difficult for paint or stain to adhere to the wood and/or penetrate the oily residue left behind from the preservative treatment. Also, when wood is painted or stained to impart a desirable color, the coloration is only imparted at the surface of the wood resulting in limited permanence to weathering, scratching or wear.

SUMMARY OF THE INVENTION

An improved process for preparing water-soluble copper salts of carboxylic acids is described. More particularly, the improved process comprises the steps of
 (A) providing a mixture comprising
  (A-1) as a copper source, copper metal, a copper oxide or mixtures thereof,
  (A-2) at least one organic monocarboxylic acid containing at least about 10 carbon atoms,
  (A-3) at least one alkanolamine compound characterized by the formula $R_1(R_2)NH$ wherein $R_1$ is a hydroxyalkyl group and $R_2$ may be hydrogen or a hydroxyalkyl group, and (A-4) water, (B) treating the mixture with oxygen at a temperature up to about the reflux temperature of the mixture until the desired water-soluble copper salt is obtained, and (C) recovering the copper salt as an aqueous solution. The mixture (A) can be modified to include one or more dyes to produced colored solutions of the water-soluble metal salts. The water-soluble copper salts prepared in accordance with the method of the invention are useful in a variety of applications, particularly as a preservative for wood. The invention also relates to wood which has been treated with the water-soluble copper salts of the present invention.

DESCRIPTION OF THE PREFERRED EMBODIMENTS

The present invention is concerned witn the preparation of water-soluble copper salts of carboxylic acids. The method of preparing such water-soluble copper salts comprises the steps of (A) providing a mixture comprising
(A-1) as a copper source, copper metal, a copper oxide or mixtures thereof,
(A-2) at least one organic monocarboxylic acid containing at least about 10 carbon atoms,
(A-3) at least one alkanolamine compound characterized by the formula $R_1(R_2)NH$ wherein $R_1$ is a hydroxyalkyl group and $R_2$ may be hydrogen or a hydroxyalkyl group, and (A-4) water, (B) treating the mixture with oxygen at a temperature up to about the reflux temperature of the mixture until the desired water-soluble copper salt is obtained, and (C) recovering the copper salt as an aqueous solution.

The copper source utilized in the method of the present invention may comprise copper metal, a copper oxide including the hydroxide, or mixtures thereof. Generally, more preferably, the copper source is copper powder. Cuprous oxide also may be utilized.

The organic monocarboxylic acids used in the preparation of the copper salts of the present invention generally contain at least about 10 carbon atoms and may contain as many as 30 carbon atoms. Useful carboxylic acids also are characterized as having an acid number of from about 125 to about 326. The carboxylic acids from which suitable copper salts can be prepared include aliphatic, cycloaliphatic and aromatic mono- and polybasic carboxylic acids containing 10 or more carbon atoms. The organic carboxylic acids can be either natural or synthetic or mixtures thereof. The examples of natural acids, although usually refined, include straight and branched chain carboxylic acids and mixtures such as tall oil acids and cyclic carboxylic acids such as naphthenic acids. A variety of synthetic carboxylic acids, and particularly aliphatic carboxylic acids or mixtures thereof is useful.

Examples of useful organic carboxylic acids include decanoic acid, neodecanoic acid, dodecanoic acid, hexadecanoic acid, lauric acid, palmitic acid, stearic acid, oleic acid, linoleic acid, naphthenic acid, tetracosanoic acid, heptacosanoic acid, and commercially available mixtures of two or more carboxylic acids such as naphthenic, tall oil acids, rosin acids, etc.

Mixtures of two or more organic monocarboxylic acids containing at least 10 carbon atoms can be utilized in the process of the present invention, and in some instances, mixtures of at least one organic monocarboxylic acid and one or more organic monocarboxylic acid containing less than about 10 carbon atoms may be utilized in the method. In one preferred embodiment, the organic carboxylic acids utilized in the process of the invention will contain from about 10 to about 25 carbon atoms, and in another embodiment, the monocarboxylic acids used in the method of the invention may be characterized as having an acid number of from about 150 to about 250.

The mixtures which are prepared and reacted to form the water-soluble copper salts of the present invention also will contain at least one alkanolamine compound characterized by the formula $R_1(R_2)NH$ wherein $R_1$ is a hydroxyalkyl group and $R_2$ may be hydrogen or a hydroxyalkyl group. The hydroxyalkyl groups $R_1$ and $R_2$ generally are lower hydroxyalkyl groups wherein $R_1$ and $R_2$ each independently contain from 1 to about 5 carbon atoms.

Examples of alkanolamine compounds useful in the method of the present invention include ethanolamine, diethanolamine, n-propanolamine, isopropanolamine, and commercial mixtures containing one or more of said alkanolamines. A preferred alkanolamine is diethanolamine.

The relative amounts of the copper source, organic monocarboxylic acid, alkanolamine and water contained in the mixture provided in step (A) can be varied over a wide range, and the precise amounts of the various ingredients incorporated into the mixture may be varied by one skilled in the art to produce different water-soluble copper salts of carboxylic acids which may have properties which are more desirable for certain applications. For example, the amount of copper source and organic monocarboxylic acid included in the mixture may be varied to provide copper salts which may be neutral salts, acid salts or basic salts. The acid salts contain insufficient metal cation to neutralize the acid. The neutral salts contain an amount of the copper cation which is just sufficient to neutralize the acidic groups present in the salt. The basic salts contain an excess of the copper cation and are often referred to as overbased, hyperbased or superbased salts. Accordingly, in one embodiment, the copper-to-carboxylic acid equivalent ratio in the mixture provided in step (A) is from about 0.5:1 to about 15:1. In another embodiment, the copper-to-acid equivalent ratio is within the range of from about 1:1 to 15:1 and more generally from about 1:1 to about 5:1, and a still further embodiment, the copper-to-acid equivalent ratio is from about 1:1 to about 2:1.

The amount of alkanolamine included in the mixture of step (A) also may be varied, and the amount of alkanolamine is generally defined in terms of moles of alkanolamine with relation to moles of copper source. In one embodiment, the mole ratio of copper source to alkanolamine is from about 1:1 to about 1:5, and in another embodiment, the mole ratio of copper source to alkanolamine in mixture (A) is about 1:4.

The amount of water present in mixture (A) is not critical. Generally, however, sufficient water is included to provide a workable mixture and a product solution after the second step. However, the amount of water should not be excessive since this would result in a dilute solution of the desired copper salts which would generally require subsequent treatment to obtain a more concentrated salt solution.

In the second step of the process of the invention (step (B)), the mixture prepared in step (A) is treated with oxygen at a temperature up to about the reflux temperature of the mixture until the desired water-soluble copper salt is obtained. Any oxygen-supplying or containing gas can be employed as an oxygen source. Air is the most common and cheapest source of oxygen. Pure oxygen as well as mixtures of oxygen and inert gases such as nitrogen also can be used as the oxygen source.

Generally, it is advantageous that the mixture be heated to a temperature above ambient temperature to improve the rate of the reaction, and more generally, the mixture is treated with oxgyen in step (B) at a temperature of from about 70°-95° C. In one embodiment, it is preferred to heat the mixture of (A) to an elevated temperature such as from about 75° C. up to the reflux temperature prior to treating the mixture with oxygen. One advantage of this embodiment is that the tendency of the mixture to foam is significantly reduced.

As noted above, the mixture of (A) is treated with oxygen at an elevated temperature until the desired water-soluble copper salt is obtained. Completion of the reaction is reached when either or both of the following conditions are achieved: all of the copper source has been dissolved, or the soluble metal content of the reaction mass reaches the desired level or reaches a maximum. Generally, there will be little or no unreacted copper source at this stage if the reacted amounts are carefully formulated. However, if any unreacted metallic source or other residues are present, they can be removed by filtration. The soluble metal content of the reaction mixture can be determined by analysis of aliquots as the reaction proceeds.

At the end of the reaction, the desired copper salt is recovered as an aqueous solution. As mentioned, if the aqueous product contains suspended solids, either due to the presence of unreacted starting materials or to impurities contained in the commercial materials utilized in the reaction. Solid materials can be removed by filtration such as through a filter aid.

The concentration of copper salt in the aqueous solutions recovered in the process of the invention can vary over a wide range depending upon the amounts of the various reactants utilized in the reaction, and the amount of water included in the reaction mixture. The copper salt content of the recovered solution can be modified as desired by either adding additional water or removing some of the water to obtain more concentrated solutions of the desired salts. In one embodiment, the copper salt solutions prepared in accordance with the process of the present invention will contain from about 4 to about 10% or more of copper.

The mixtures prepared in step (A) of the method of the present invention also may include other ingredients for modifying the properties and characteristics of the copper salts. For example, when colored products are desired, the mixture prepared in step (A) may contain at least one dye. The choice of dye or dyes to be included in the mixture will be dictated by the color desired to be imparted to the aqueous solution of the copper salts as well as the color desired for the product treated with the aqueous copper salts of the present invention such as wood. Generally, mixtures of dyes will be utilized to provide the desired colors. In addition to being compatible with one another, tthe various dyes in a mixture must also be compatible with the mixture prepared in step (A).

A wide variety of dyes and combinations of dyes can be utilized in the present invention. The dyes may be any of the solvent, disperse and/or vat dye classes including the azo dyes, disazo dyes, the anthraquinone dyes, the pyrazalone dyes, the quinophthalone dyes, the phthalocyanine dyes and metal complex dyes. It is preferred that the dyes be soluble in the mixture prepared in step (A) and/or soluble in the aqueous solution of the copper salts prepared in accordance with the method of the invention. Examples of useful dyes include, but are not limited to the following:

Solvent Black 3
Solvent Black 7
Solvent Blue 70
Solvent Blue 101
Solvent Blue 59
Solvent Blue 128
Solvent Blue 58
Solvent Blue 102
Solvent Blue 59
Solvent Blue 35
Solvent Blue 36
Solvent Green 2
Solvent Green 3
Solvent Green 20
Solvent Green 23
Solvent Green 24
Solvent Green 25
Solvent Green 26
Solvent Green 28
Disperse Orange 25
Solvent Orange 60
Solvent Orange 3
Solvent Orange 56
Solvent Red 1
Disperse Red 22
Solvent Red 24
Solvent Red 26
Disperse Red 60
Solvent Red 111
Solvent Red 135
Solvent Red 209
Solvent Red 210
Solvent Red 169
Solvent Red 207
Solvent Red 195
Solvent Red 109
Solvent Red 172
Solvent Red 138
Solvent Red 168
Vat Red 1
Vat Red 41
Solvent Yellow 3
Solvent Yellow 30
Solvent Yellow 33
Solvent Yellow 77
Solvent Yellow 93
Solvent Yellow 105
Solvent Yellow 114
Solvent Yellow 163

Solvent Yellow 18
Solvent Yellow 109
Solvent Yellow 72
Solvent Yellow 33
Solvent Yellow 43
Solvent Yellow 79
Solvent Yellow 14
Solvent Yellow 16
Solvent Yellow 129
Solvent Violet 13
Solvent Violet 14
Solvent Violet 26
Solvent Violet 38

The above dye types are available from a variety of commercial sources under a variety of names. For example, Morfast Brown 100, Morfast Black 101, Morfast Yellow 101 and Morfast Blue 105 are commercially available from Morton Thiokol, Inc., Morton Chemical Div.; Brown D, Jet Black, Wood Black are useful dyes available from Bruce Chemical Company.

The dye or dyes are generally incorporated into the mixture prepared in step (A) prior to the treatment of the mixture with oxygen. Inclusion of the dyes into the reaction mixture, as opposed to the addition of the dyes after completion of the reaction, provides a more stable colored solution of the copper salt. The colored solutions of the present invention exhibit good stability, and as will be discussed more fully below can be utilized to penetrate various substrates such as wood and to impart desirable color characteristics to the treated substrates.

Other ingredients may be included in the mixture as prepared in step (A) prior to treatment with oxygen to impart other desirable properties. For example, the mixture prepared in step (A) may include liquid mold growth inhibitors which are non-toxic. Examples of such inhibitors include various glycols such as ethylene glycol, propylene glycol, butylene glycol, etc. The glycols are easily blended into the mixture and are retained in the aqueous solutions of the copper salts. The amount of glycol incorporated into the mixture may be varied over a wide range, and up to about 2 to 3 moles of glycol may be included per mole of monocarboxylic acid contained in the mixture.

Anti-foam agents also may be included in the aqueous mixtures to reduce the amount of foaming which occurs during the reaction as the oxygen is passed through the reaction mixture. The choice of anti-foam agents generally is not critical, and a desirable antifoam agent in a particular mixture can be determined readily by one skilled in the art.

In another embodiment, the aqueous solutions of copper salts prepared in accordance with the present invention may be diluted or concentrated to provide solutions containing particular concentrations of copper. The solutions generally prepared in accordance with the method of the present invention may contain up to about 10% by weight of copper, and more generally will contain from about 4 to about 8% copper. The concentration of copper in the aqueous solution can be reduced to desired levels by dilution with water or other solvents such as alcohols and glycols. The choice of diluent solvent is not critical so long as the diluent solvent is compatible with the copper salt and does not interfere with the intended use of the aqueous solution.

The following examples illustrate the method of the present invention for preparing copper salts of monocarboxylic acids. Unless otherwise indicated in the following examples and elsewhere in the specification and claims, all parts and percentages are by weight, and all temperatures are in degrees centigrade.

EXAMPLE 1

A mixture is prepared comprising the following ingredients in the order indicated: 325 parts of crude naphthenic acid from Merichem Company, having an acid number of 179 (molecular weight 313, 1.04 equivalents) 608 parts of crude naphthenic acid having an acid number of 144 (molecular weight 390, 1.55 equivalents) obtained from Gulf Oil Company, 841 parts (8 equivalents) of diethanolamine, 30 parts of dye mixture containing equal parts of Morfast Brown 100, Brown D and Interplast Brown 2RL Crompton and Knowles Corp., Industrial Products Div., 127 parts (4 equivalents) of copper powder, and 100 parts of water. The mixture is heated to about 80° C. and sparged with air at a rate of two cubic feet per hour until all of the copper has reacted which is about 16 hours. The reaction mixture is cooled and recovered.

EXAMPLE 2

The procedure of Example 1 is repeated except that the reaction mixture contains 300 parts of water.

EXAMPLE 3

A mixture of 667 parts (2.7 equivalents) of naphthenic acid from Exxon which are treated with 2% Filtrol and filtered (acid number 227 and molecular weight about 247), 10 parts of Morfast Brown 100, 7.5 parts of Brown D, 10 parts of Interplast Brown 2RL, 945 parts (9 moles) of diethanolamine, 127 parts (4 equivalents) of copper powder in 100 parts of water is prepared. Air is bubbled through the mixture at about 7–8 cubic feet per hour as the mixture is heated to about 83° C. over a period of about 4 hours. The mixture is maintained at a temperature of 80°–85° C. for an additional 4 hours to produce the desired water-soluble, brown copper salt.

EXAMPLE 4

A mixture of 469 parts (1.88 moles) of naphthenic acid from Exxon treated as described in Example 3, 242 parts (0.62 mole) of crude Gulf naphthenic acid, 600 parts of water, 10 parts of Morfast Brown 100, 7.5 parts of Brown D, 10 parts of Interplast Brown, 560 parts (9.2 moles) of monoethanolamine, 120 parts (3.8 equivalents) of copper powder and 0.2 part of anti-foam agent (General Electric 66) is prepared and air is bubbled through the mixture at a rate of about 7 cubic feet per hour as the mixture is heated to a temperature of about 77° C. over a period of 1.5 hours. The mixture is maintained at a temperature of between 76 and 78° C. for an additional 3 hours whereupon the mixture is cooled and the desired brown solution of the copper salt is recovered.

EXAMPLE 5

A mixture of 409 parts (1.56 equivalents) of crude naphthenic acid from Exxon, 407 parts (1.04 equivalents) of crude naphthenic acid from Gulf Oil, 40 parts of Morfast Yellow 101, 15 parts of Morfast Blue 105, 124 parts (4 equivalents) of copper powder, 420 parts of water, 0.25 part of anti-foam agent (General Electric 66) and 550 parts (9 moles) of monoethanolamine is prepared. Air is bubbled through the mixture at a rate of about 7–8 cubic feet per hour as the mixture is heated to a temperature of about 88° in two hours. The mixture is maintained at a temperature of between 82°–88° C. for the next 80 minutes. The mixture is cooled, and 100 parts of isopropyl alcohol are added. A dark-green solution of the desired copper salt is recovered. This solution can be diluted to 2%, 1%, 0.5% and 0.1% copper, and no solid precipitates are observed.

EXAMPLE 6

A mixture of 666 parts (2.66 equivalents) of crude Exxon naphthenic acid, 258 parts (0.67 equivalents) of crude Gulf naphthenic acid, 160 parts of copper powder, 13 parts of Morfast Brown 100, 10 parts of Brown D, 13 parts of Interplast 2LR, 280 parts of water, 0.5 part of anti-foam agent (General Electric 66) and 702 parts (11.5 moles) of monoethanolamine is prepared. Air is bubbled through the mixture at a rate of about 8 CFH as the temperature of the mixture is raised to about 92° C. over a period of about 2 hours. The mixture then is maintained at a temperature in the range of 78.5°-92° C. for a period of about 2 hours as air is continuously bubbled through the mixture. At the end of this time, the mixture is cooled and the product is recovered.

EXAMPLE 7

A mixture of 500 parts (2 moles) of crude Exxon naphthenic acid, 515 parts (1.33 moles) of crude Gulf naphthenic acid, 381 parts (5 moles) of propylene glycol, 13 parts of Morfast Brown 100, 10 parts of Brown D, 13 parts of Interplast Brown 2LR, 160 parts (2.52 moles) of copper powder, 300 parts of water, 0.5 part of anti-foam agent (General Electric 66) and 702 parts (11.5 moles) of monoethanolamine is prepared in the reaction vessel. The air is bubbled through the mixture at a rate of about 8 CFH as the temperature of the mixture is raised to 90° C. over a period of 80 minutes and maintained at a temperature between 81° C. and 93° C. for an additional period of 2.5 hours. The reaction product then is cooled and recovered. The brown aqueous solution contains 5.99% copper.

EXAMPLE 8

A mixture of 608 parts (2.43 moles) of Exxon naphthenic acid treated as in Example 3, 105 parts (0.27 mole) of crude Gulf naphthenic acid, 10 parts of Morfast Brown 100, 7.5 parts of Brown D, 10 parts of Interplast Brown 2RL, 500 parts of water, 127 parts (2 moles) of copper powder and 610 parts (10 moles) of monoethanolamine is prepared in the reaction vessel. Air is bubbled through the mixture at a rate of about 7 CFH as the temperature of the mixture is raised to a temperature of about 68° C. over a period of 3 hours, and the mixture is maintained at a temperature between 58°-68° C. for an additional 3.5 hours. The mixture is cooled and the reaction product is recovered.

EXAMPLE 9

A mixture of 675 parts (2.7 moles) of Exxon naphthenic acid treated as in Example 3, 127 parts (2 moles) of copper powder, 10 parts of Morfast Brown 100, 7.5 parts of Brown D, 10 parts of Interplast Brown 2LR, 500 parts of water, 610 parts (10 moles) of monoethanolamine and 0.2 part of anti-foam agent (General Electric 66) is prepared in the reaction vessel. Air is bubbled through the mixture at a rate of about 7 CFH as the mixture is heated to a temperature of about 79.5° C. ove a period of 1.5 hours. The air rate is reduced to 5 CFH as the temperature of the reaction mixture is maintained in the range of 79.5°-67° C. for 3.5 hours. The mixture is cooled, and a brown reaction product is recovered.

EXAMPLE 10

A mixture of 778 parts (3 moles) of crude Exxon naphthenic acid, 8.2 parts of Morfast Black 101, 8.2 parts of Brown D, 39.5 parts of Jet Black, 127 parts (2 moles) of copper powder, 400 parts of water and 550 parts (9 moles) of monoethanolamine is prepared. Air is bubbled through the mixture at a rate of about 7-8 CFH as the mixture is heated to a temperature of about 82° C. over a period of about 2 hours. The temperature of the mixture then is maintained at between 82°-75° C. for an additional 3 hours. The mixture is cooled and the desired black solution is recovered.

EXAMPLE 11

The general procedure of Example 10 is repeated except that 76 parts (1 mole) of propylene glycol are included in the reaction mixture prior to air blowing.

EXAMPLE 12

A mixture of 1036 parts (4 moles) of crude Exxon naphthenic acid, 25 parts of Morfast Black 101, 25 parts of Morfast Brown 100 and 40 parts of Jet Black (Bruce Company), 950 parts of water, 196 parts (3 moles) of copper powder and 860 parts (14.1 moles) of monoethanolamine is prepared. Air is bubbled through the mixture at a rate of about 7-8 CFH as the mixture is heated to about 83.5° C. in about 2 hours. The mixture then is maintained at a temperature of from about 83.5 and 73° C. for an additional 3 hours for a total reaction time of about 5 hours. At the end of about 2.5 hours of the reaction, an additional 6 parts of Jet Black were added to the reaction mixture.

EXAMPLE 13

A mixture of 777 parts (3 moles) of crude Exxon naphthenic acid, 5.4 parts of Morfast Black 101, 5.4 parts of Interplast Brown 2LR, 42 parts of Wood Black (Bruce Company), 127 parts (2 moles) of copper powder, 550 parts of water and 550 parts (9 moles) of monoethanolamine is prepared. Air is bubbled through the mixture at a rate of about 7-8 CFH as the temperature of the mixture is raised 84° C. in one hour. The mixture then is maintained at between 84 and 71° C. for an additional 3.75 hours. A stable black solution of the copper salt is recovered and the solution can be diluted to a copper concentration of about 0.5% with water. The diluted solution also is stable.

EXAMPLE 14

A mixture of 420 parts (1.62 moles) of crude Exxon naphthenic acid, 418 parts (1.08 moles) of crude Gulf naphthenic acid, 9.1 parts of Morfast Black 101, 7.3 parts of Brown D, 20 parts of Jet Black, 20 parts of Wood Black, 127 parts (2 moles) of copper powder, 200 parts of water, 990 parts (8 moles) of an 85% aqueous solution of diethanolamine and two drops of anti-foam agent is prepared. Air is bubbled through the mixture at a rate of about 7-8 CFH as the temperature of the mixture is raised to about 68° C. in one hour and thereafter to a temperature of 81.5° in 1.5 hours. The mixture then is maintained at between 77.5 and 84° C. for about 4.5 hours. After cooling overnight, the mixture is again reheated to about 76°-84.5° C. for an additional hours. After cooling overnight again, the mixture is reheated to about 80° C. for 1.75 hours. The product is recovered as an aqueous solution which contains about 5.86% copper.

EXAMPLE 15

A mixture of 420 parts (1.62 moles) of crude Exxon naphthenic acid, 420 parts (1.08 moles) of crude Gulf naphthenic acid, 12.5 parts of Morfast Black 101, 42 parts of Wood Black, 127 parts (2 moles) of copper powder, 200 parts of water, 840 parts (8 moles) of diethanolamine and two drops of anti-foam agent is prepared. Air is bubbled through the mixture at a rate of about 7-8 CFH as the temperature of the mixture is raised to 82.5° C. in 3 hours. The mixture is maintained at about this temperature for an additional 3.25 hours. After cooling overnight, the mixture is reheated to a temperature of about 68°-98° C. for an additional 4 hours. The mixture is cooled and the desired product is recovered.

EXAMPLE 16

A mixture of 545 parts (1.35 moles) of crude Gulf naphthenic acid, 210 parts (0.81 mole) of crude Exxon naphthenic acid, 184 parts (0.54 mole) of naphthenic acid distillation bottoms, 14.6 parts of Interplast Brown 2LR, 10.5 parts of Jet Black, 10.5 parts of Wood Black, 127 parts (2 moles) of copper powder, 468 parts of water and 488 parts (8 moles) of monoethanolamine is prepared. Air is bubbled through the mixture at a rate of about 7-8 CFH as the mixture is heated to a temperature of about 80.5° C. in 1.5 hours. The mixture then is maintained at between 70°-83° C. for an additional 4 hours. After cooling, the desired product is recovered.

EXAMPLE 17

A mixture of 655 parts (1.62 moles) of crude Gulf naphthenic acid, 280 parts (1.08 moles) of crude Exxon naphthenic acid, 10.4 parts of Morfast Black 101, 10.4 parts of Morfast Yellow 101, 10.4 parts of Brown D, 42 parts of a Jet Black and Wood Black mixture (Bruce Company), 127 parts (2 moles) of copper powder, 400 parts of water and 488 parts (8 moles) of monoethanolamine is prepared. Air is bubbled through the mixture at a rate of about 7-8 CFH as the temperature of the mixture is raised to 75° C. in 0.5 hour and 85° C. in one hour. The mixture is maintained between 77°-85° C. for an additional 3 hours. After cooling, the desired product is recovered.

EXAMPLE 18

A mixture of 325 parts (1.04 moles) of Merichem crude naphthenic acid, 585 parts (1.54 moles) of crude Gulf naphthenic acid, 841 parts (8 moles) of diethanolamine, 127 parts (2 moles) of copper powder, 100 parts of water and 0.5 parts of anti-foam agent is prepared and heated to a temperature of 184° F (about 84° C.). The air is then bubbled through the mixture, initially at a rate of 2 CFH. After about 15 minutes, the temperature of the mixture is raised to about 90° C. and the air rate is increased to 3 CFM. In another 15 minutes, the mixture is raised to about 94° C. and the air rate is increased to 6 CFM. Over the next 45 minutes, the temperature of the reaction mixture is lowered to about 90° C. and the air rate increased to 8 CFM. The mixture then is maintained at a temperature of about 90° C. for an additional 6 hours while blowing with air at a rate of between 8-9 CFH. The reaction mixture is recovered and is found to contain about 6.4% copper. The green solution can be cut back to a copper concentration of about 6.1% by the addition of water.

The water-soluble copper salts of carboxylic acids prepared in accordance with the method of the present invention may be utilized in a variety of applications and end uses wherein water-solubility is desired. For example, the water-soluble copper salts can be utilized as preservatives in water-based paints, and the preparation of aqueous systems utilized as a preservative for treating wood, fabrics, cordage and other fibrous materials. When dyes are included in the mixtures utilized in the formation of the copper salts of the present invention, the products can be utilized also to impart desired color characteristics to various substrates such as wood, fabrics, cordage and other fibrous materials.

As mentioned earlier, there is a growing need for wood which is both acceptable to society from an aesthetic standpoint and protected from wood-destroying organisms. It has now been discovered that when the aqueous compositions containing the copper salts of the present invention are prepared in the presence of one or more dyes, the color of the aqueous solution can be controlled and modified as desired, and when such colored aqueous solutions are used to impregnate wood, the treated wood is protected against wood-destroying organisms and has the desirable aesthetic appearance. Because the dyes are soluble in the solution, the process of the present invention wherein wood is contacted with the aqueous compositions of the present invention, results in deeper penetration of the color into the wood, and longer lasting colors.

When the aqueous copper salt solutions of the present invention are to be used for the preservation of wood, the solutions generally are diluted with water, alcohol or water-alcohol mixtures to provide concentrations of the copper salt in the working solutions such that the working solution will contain from about 0.5% w to about 2 to 3% w of copper and more generally from about 0.8 to 1.2 w% or about 1 w% of copper.

The solutions of the water-soluble copper salts of the present invention also may contain other additives and components which improve the properties or performance of the solutions and/or which impart desirable properties to the treated wood. For example, the aqueous solutions may contain anti-foam agents, flame-retardant compositions, insecticides, odorants, moldicides, wood stabilizing agents, etc. When included in the water solutions of the present invention, such additives may be present in amounts ranging from about 0 01 to about 20-30%. The amount of such additives included in the solutions of the invention may vary over a wide range although amounts of from about 0.01 to about 5% of these additives generally are satisfactory.

Inorganic fire retardant compositions are particularly useful in the compositions of the invention. Examples of inorganic materials include metal oxides which are well known in the art such as antimony oxide, etc. Examples of organic fire retardants include a number of halogenated and organophosphorus compounds which may be dispersed in the solutions.

Insecticides also can be included in the solutions of the invention, and it is preferable that the insecticide be soluble or dispersible in the working solutions of this invention. Examples of such insecticides include Ficam 76WP available from BFC Chemicals, Inc. and permethrin available from Mooney Chemicals under the trade designation M-GARD W320 TM.

Odorants can be included in the solutions of the invention, and one preferred odorant is pine oil. Other compounds having desired odors can be included in the solutions.

Wood-stabilizing agents may be included in the aqueous solutions of the invention to provide the wood with improved dimensional stability. Such agents remain in the cell walls when the wood is dried, and this bulking action prevents the wood from shrinking. Various chemicals have been suggested for this purpose in the art of wood treating. A useful group of stabilizing agents are the polyalkylene glycols, and more particularly, the polyethylene glycols. The molecular weight of the glycols should be selected so that the glycols are soluble in water. Thus, polyethylene glycols having molecular weights of up to about 6000 are desirable because these generally are water-soluble. Various of these polyethylene glycols are available commercially.

Carbowax-type wetting agents which are polyethylene glycols having different molecular weights are useful as wood stabilizers. For example Carbowax No. 1000 has a molecular weight range of from about 950 to 1050 and contains from 20 to 24 ethoxy units per molecule. Carbowax No. 4000 has a molecular weight range of from about 3000 to 3700 and contains from 68 to 85 ethoxy units per molecule.

The method of the present invention for preserving wood comprises contacting the wood with the solutions of the invention comprising the copper salt and one or more of the optional additives described above for a period of time sufficient to enable the desired amount of copper salt to penetrate into the wood to a depth which is sufficient to provide the wood with the desired preservative properties. The contact between the wood and the solutions of the present invention can be effected by brushing, spraying, painting, immersing, etc. Preferably, contact between the wood and the solutions of the present invention is effected by immersing the wood in the mixture for a period of time which is sufficient to obtain the desired result.

In one method of the present invention, the aqueous solutions in which the wood is immersed can be maintained at a temperature of from about 5° to about 95° C. at atmospheric pressure. However, the method of the invention can be carried out at ambient temperature thereby eliminating the need for any equipment or materials for heating or cooling the aqueous solutions. In some instances, it may be advantageous to heat the aqueous solutions to elevated temperatures to increase the rate of penetration.

The method of the invention also can be conducted on wood contained in an enclosed vessel under vacuum or pressure conditions or a combination thereof. The use of pressure for improving the penetration of various chemicals into all types of wood is well known in the art. In this technique, the wood is placed in a chamber which is sealed and evacuated in a regulated cycle which is related to and determined from a consideration of the species of wood. Generally, the period of evacuation will vary from about 15 minutes to one hour, and the pressure within the sealed chamber is about two inches of mercury or less. The purpose of this step is to remove air and wood volatiles from the wood. The solutions of the present invention then are introduced into the enclosed container, and the amount of the solution should be sufficient to immerse the wood completely. The temperature of the solution is adjusted to at least about ambient temperature and preferably to about 75°–250° F. The pressures utilized in the pressure method can be as high as 250 psig., and are generally from about 50 to 150 psig. Pressurization of the vessel then is initiated, and the pressure is maintained at a desired level for a given period of time. Initially, the pressure within the vessel may decrease as the mixture within the container penetrates into the wood. The pressure may be raised to maintain a desirable level throughout the penetration period of treatment. Stabilization of the pressure within the vessel is an indication that there is no longer any penetration of the liquid into the wood. At this point, the pressure can be released, the vessel drained, and the wood removed. The details of the pressure process, including pressure ranges, concentration of the treating mixture and the cycling of vacuum and pressure can be readily determined by one skilled in the art.

The aqueous copper salt solutions of the invention can be used for preserving a wide variety of wood types. The actual time of contact of the wood with the solutions will vary depending on a variety of factors such as, for example, (1) the level of pressure within the vessel, (2) the amount of metal salt to be introduced into the wood, (3) the difficulty of penetration into the particular type of wood being treated, and (4) whether the wood is partially seasoned or dry wood. Any type of wood, dry or partially seasoned, can be treated with the compositions of the invention. Examples of wood species which can be treated with the compositions of the invention include Southern Yellow Pine, Western Red Cedar, Douglas fir, Hemlock, Ash, White Pine, Red Pine, Birch, Red Oak, Beech, etc.

The following are specific examples of the aqueous wood-treating solutions of the invention.

|  | Amount (Pbw) |
|---|---|
| Example A (2% Cu) | |
| Solution from Example 1 | 100 |
| Water | 200 |
| Example B (2% Cu) | |
| Solution from Example 2 | 100 |
| Water | 200 |
| Example C (0.5% Cu) | |
| Solution from Example 3 | 100 |
| Water | 1280 |
| M-Gard W320 | 100 |
| Example D (0.5% Cu) | |
| Solution from Example 18 | 100 |
| Water | 1180 |
| PEC 1000 | 50 |
| Example E (2% Cu) | |
| Solution from Example A | 100 |
| n-octyl-4-isothiazolinone | 0.2 |

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A method of preparing water-soluble copper salts of carboxylic acids comprising the steps of
  (A) providing a mixture comprising
    (A-1) as a copper source, copper metal, a copper oxide or mixtures thereof,
    (A-2) at least one organic monocarboxylic acid containing about 10 to about 30 carbon atoms,
    (A-3) at least one alkanolamine compound characterized by the formula $R_1(R_2)NH$ wherein $R_1$ is a hydroxyalkyl group and $R_2$ may be hydrogen or a hydroxyalkyl group, and
(A-4) water,
(B) treating the mixture with oxygen at a temperature up to about the reflux temperature of the mixture until the desired water-soluble copper salt is obtained, and
(C) recovering the copper salt as an aqueous solution.

2. The method of claim 1 wherein the copper source (A-1) is copper metal.

3. The method of claim 1 wherein the organic monocarboxylic acid (A-2) contains from about 10 to about 30 carbon atoms.

4. The method of claim 1 wherein $R_1$ and $R_2$ in the alkanolamine are hydroxyalkyl groups.

5. The method of claim 1 wherein the hydroxy alkyl groups $R_1$ and $R_2$ each independently contain from 1 to about 5 carbon atoms.

6. The method of claim 1 wherein the mixture prepared in step (A) is heated to about reflux temperature and then treated with oxygen for a period of time sufficient to produce the desired copper salt.

7. The method of claim 1 wherein the alkanolamine (A-3) is ethanolamine.

8. The method of claim 1 wherein the alkanolamine (A-3) is diethanolamine.

9. The method of claim 1 wherein the monocarboxylic acid (A-2) is characterized as having an acid number of from about 150 to about 250.

10. The method of claim 1 wherein the mixture prepared in step (A) contains a copper source and the monocarboxylic acid in amounts sufficient to provide a metal to acid equivalent ratio of from about 1:1 to 15:1.

11. The method of claim 1 wherein the mole ratio of copper source to alkanolamine in the mixture (A) is from about 1:1 to about 1:5.

12. The method of claim 1 wherein the mole ratio of copper source to alkanolamine in mixture (A) is about 1:4.

13. The method of claim 1 wherein the mixture is treated with oxygen in step (B) at a temperature of from about 70°–95° C.

14. The method of claim 1 wherein the organic carboxylic acid (A-2) is naphthenic acid.

15. The method of claim 1 wherein the mixture of (A) also contains at least one organic dye (A-5).

16. A method of preparing water-soluble copper salts of carboxylic acids comprising the steps of
(A) providing a mixture comprising
(A-1) as a copper source, copper metal, a copper oxide or mixtures thereof,
(A-2) at least one organic monocarboxylic acid containing at least about 10 to about 30 carbon atoms,
(A-3) at least one dialkanolamine, and
(A-4) water,
(B) treating the mixture with oxygen while maintaining the mixture at a temperature up to about the reflux temperature of the mixture until the desired water-soluble copper salt is obtained, and
(C) recovering the copper salt as an aqueous solution.

17. The method of claim 15 wherein the copper source is copper metal.

18. The method of claim 16 wherein the monocarboxylic acid (A-2) contains from about 10 to about 20 carbon atoms.

19. The method of claim 16 wherein the organic monocarboxylic acid (A-2) is a naphthenic acid.

20. The method of claim 16 wherein the dialkanolamine (A-3) is diethanolamine.

21. The method of claim 16 wherein the equivalent ratio of (A-1) to (A-2) is from about 1:1 to about 5:1 and the mole ratio of (A-1) to (A-3) is from about 1:2 to about 1:5.

22. The method of claim 16 wherein the mole ratio of (A-1) to (A-3) is about 1:4.

23. The method of claim 16 wherein the mixture of (A) is heated up to a temperature of about 75°–90° C., and the mixture is then treated with oxygen until the desired water-soluble copper salt is obtained.

24. The method of claim 16 wherein the mixture (A) also contains at least one organic dye (A-5).

25. A method of preparing water-soluble copper salts of naphthenic acids which comprises the steps of
(A) providing a mixture comprising
(A-1) copper metal,
(A-2) at least one naphthenic acid,
(A-3) diethanolamine, wherein the equivalent ratio of copper to acid is from about 1:1 to about 2:1 and the mole ratio of copper to diethanolamine is about 1:4, and
(A-4) water,
(B) treating the mixture with oxygen at a temperature of from about 75° C. up to about the reflux temperature of the mixture for a period of time sufficient to form the desired water-soluble copper naphthenic salt, and
(C) recovering the copper salt as an aqueous solution.

26. The water-soluble copper salt prepared in accordance with the method of claim 1.

27. The water-soluble copper salt prepared in accordance with the method of claim 16.

28. The water-soluble copper salt prepared in accordance with the method of claim 25.

29. A method of preserving wood which comprises contacting the wood with an effective amount of the aqueous solution of a copper salt prepared in claim 1.

30. A method of preserving wood which comprises contacting the wood with an effective amount of the aqueous solution of a copper salt prepared in claim 16.

31. A method of preserving wood which comprises contacting the wood with an effective amount of the aqueous solution of a copper salt prepared in claim 25.

32. Wood treated in accordance with the method of claim 29.

33. Wood treated in accordance with the method of claim 30.

34. Wood treated in accordance with the method of claim 31.

* * * * *